(12) United States Patent
Ryu et al.

(10) Patent No.: US 10,416,323 B2
(45) Date of Patent: Sep. 17, 2019

(54) RADIATION IMAGING APPARATUS, RADIATION IMAGING SYSTEM, AND METHOD OF OPERATING RADIATION IMAGING APPARATUS

(71) Applicant: CANON KABUSHIKI KAISHA, Tokyo (JP)

(72) Inventors: Takuya Ryu, Kokubunji (JP); Tomoyuki Yagi, Chofu (JP); Katsuro Takenaka, Honjo (JP); Hideyuki Okada, Honjo (JP); Eriko Sato, Tokyo (JP); Shinichi Takeda, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 266 days.

(21) Appl. No.: 15/446,187

(22) Filed: Mar. 1, 2017

(65) Prior Publication Data

US 2017/0285189 A1    Oct. 5, 2017

(30) Foreign Application Priority Data

Mar. 29, 2016  (JP) .................................. 2016-066316
Jul. 7, 2016   (JP) .................................. 2016-135207

(51) Int. Cl.
    *H05G 1/64*     (2006.01)
    *G01T 1/24*     (2006.01)
    (Continued)

(52) U.S. Cl.
    CPC .............. *G01T 1/247* (2013.01); *A61B 6/487* (2013.01); *A61B 6/54* (2013.01); *G01N 23/043* (2013.01); *H04N 5/32* (2013.01); *H04N 5/361* (2013.01)

(58) Field of Classification Search
    CPC ......... A61B 6/487; A61B 6/54; A61B 6/4233; A61B 6/06; A61B 6/4488; A61B 6/032;
    (Continued)

(56) References Cited

U.S. PATENT DOCUMENTS 7,227,926 B2    6/2007   Kameshima et al. ....... 378/98.9
7,381,963 B2    6/2008   Endo et al. .............. 250/370.09
(Continued)

FOREIGN PATENT DOCUMENTS

EP    2442557 A2       4/2012
JP    2010-227511 A   10/2010
(Continued)

OTHER PUBLICATIONS

Extended European Search Report dated Jul. 13, 2017 in counterpart EP application No. 17159306.4 (English).

*Primary Examiner* — Irakli Kiknadze
(74) *Attorney, Agent, or Firm* — Venable LLP (57) ABSTRACT

A radiation imaging apparatus includes a pixel array, a scanning circuit for scanning a plurality of rows of the pixel array in accordance with a selected mode of a plurality of modes, and a readout circuit configured to read out signals from pixels on a selected row in scanning by the scanning circuit. The plurality of modes include a first mode of performing image capturing at a first frame rate and a second mode of performing image capturing at a second frame rate lower than the first frame rate. The number of times of scanning on the plurality of rows by the scanning circuit in one frame period in the second mode is larger than that of scanning on the plurality of rows by the scanning circuit in one frame period in the first mode.

12 Claims, 7 Drawing Sheets

(51) Int. Cl.
*A61B 6/00* (2006.01)
*H04N 5/32* (2006.01)
*H04N 5/361* (2011.01)
*G01N 23/04* (2018.01)

(58) Field of Classification Search
CPC ..... A61B 6/4241; A61B 6/4405; A61B 6/482; A61B 6/508; A61B 6/4291; A61B 6/4423; A61B 6/4441; A61B 6/4028; A61B 6/4035; A61B 6/12; A61B 6/4042; A61B 90/39; A61B 6/4208; A61B 6/4225; A61B 6/542; A61B 6/563; G01N 23/043; G01T 1/247; G01T 1/17; G01T 1/2018; G01T 1/202; G01T 1/2971; H04N 5/32; H04N 5/361; H01J 35/14
USPC .......................................... 378/19, 62, 98, 8
See application file for complete search history.

(56) References Cited

U.S. PATENT DOCUMENTS

| | | | |
|---|---|---|---|
| 7,386,089 B2 | 6/2008 | Endo et al. | 378/5 |
| 7,466,345 B2 | 12/2008 | Kameshima et al. | 348/220.1 |
| 7,476,027 B2 | 1/2009 | Takenaka et al. | 378/207 |
| 7,514,663 B2 | 4/2009 | Yagi et al. | 250/208.1 |
| 7,532,706 B2 | 5/2009 | Kameshima et al. | 378/98 |
| 7,696,484 B2 | 4/2010 | Yokoyama et al. | 250/370.09 |
| 7,839,977 B2* | 11/2010 | Kameshima | A61B 6/4233 |
| | | | 250/370.09 |
| 7,965,817 B2 | 6/2011 | Kameshima et al. | 378/98.8 |
| 7,994,481 B2 | 8/2011 | Yagi et al. | 250/370.09 |
| 8,072,514 B2 | 12/2011 | Takenaka et al. | 348/246 |
| 8,541,754 B2 | 9/2013 | Takenaka et al. | |
| 8,809,795 B2 | 8/2014 | Takenaka et al. | G01T 1/2928 |
| 9,048,143 B2 | 6/2015 | Takenaka et al. | |
| | | | H01L 27/14612 |
| 9,134,432 B2 | 9/2015 | Iwashita et al. | G01T 1/16 |
| 2010/0148080 A1 | 6/2010 | Endo et al. | 250/370.08 |
| 2010/0246770 A1* | 9/2010 | Niwa | G01T 1/2018 |
| | | | 378/98 |
| 2011/0317054 A1 | 12/2011 | Kameshima et al. | 348/302 |
| 2015/0078530 A1* | 3/2015 | Hawver | A61B 6/4225 |
| | | | 378/98 |
| 2015/0226865 A1* | 8/2015 | Nishihara | H01L 27/14609 |
| | | | 250/366 |
| 2015/0293238 A1 | 10/2015 | Iwashita et al. | G01T 1/24 |
| 2017/0014094 A1* | 1/2017 | Hiroshige | A61B 6/4233 |
| 2017/0156687 A1* | 6/2017 | Hosoki | H04N 5/32 |

FOREIGN PATENT DOCUMENTS

| | | |
|---|---|---|
| JP | 2010-268171 A | 11/2010 |
| JP | 2011-045492 A | 3/2011 |
| JP | 2014-108284 | 6/2014 |
| WO | WO 2011/024448 A1 | 3/2011 |
| WO | WO 2011/027538 A1 | 3/2011 |

\* cited by examiner

RADIATION IMAGING APPARATUS, RADIATION IMAGING SYSTEM, AND METHOD OF OPERATING RADIATION IMAGING APPARATUS

BACKGROUND OF THE INVENTION

Field of the Invention

The present invention relates to a radiation imaging apparatus, a radiation imaging system, and a method of operating a radiation imaging apparatus.

Description of the Related Art

Recently, as a radiation imaging apparatus used for medical imaging diagnosis or non-destructive inspection using X-rays, there has prevailed a radiation imaging apparatus using an FPD (Flat Panel Detector) formed from a semiconductor material. Such a radiation imaging apparatus can be used as a digital imaging apparatus for still image capturing such as general imaging and moving image capturing such as fluoroscopy in, for example, medical imaging diagnosis. An FPD includes a detector having a matrix of a plurality of photoelectric conversion elements which convert radiation into electrical signals and a readout circuit for reading out electrical signals from the detector.

An image obtained by the FPD includes offset components (noise components) originating from capacitance variations in the detector and offset variations in the readout circuit. There is available a method of performing image correction for the removal of offset components by obtaining an offset image by performing image readout without irradiation with radiation, obtaining a radiation image by performing readout upon irradiation with radiation, and then subtracting the offset image from the radiation image. Such image correction is called offset correction.

For offset image inclusion, there are available a scheme of reading in advance an offset image before radiation image obtaining and storing the corresponding information in advance and a scheme of obtaining an offset image immediately before or after a radiation image is obtained. When performing moving image obtaining using an FPD, the scheme of obtaining an offset image immediately before or after the acquisition of a radiation image requires an imaging interval two times and causes noise 42 times more than the scheme of obtaining an offset image in advance. Moving image capturing using an FPD has recently been required to achieve lower noise and higher frame rate. In terms of these requirements, the method of obtaining an offset image in advance is more advantageous. In such a scheme, an offset image is prepared for each image capture mode, and offset images are switched in accordance with image capture modes.

It is known that offset components transiently change immediately after image capture modes are switched. In addition, since this transient change is not high in reproducibility, it is difficult to properly correct a radiation image immediately after image capture mode switching by using an offset image obtained in advance. This leads to the superimposition of artifacts on the image.

Japanese Patent Laid-Open No. 2014-108284 discloses a technique of obtaining in advance transient offset image data for the correction of transiently changing components and correcting, for example, several radiation images immediately after image capture mode switching by using the transient offset image data.

The technique disclosed in Japanese Patent Laid-Open No. 2014-108284, however, is required to obtain transient offset image data in advance based on all image capture mode switching patterns before image capturing. It takes much time to obtain the data. In addition, an enormous amount of transient offset image data is required.

SUMMARY OF THE INVENTION

The present invention provides a technique advantageous in suppressing a deterioration in image quality immediately after mode switching.

One of aspects of the present invention provides a radiation imaging apparatus comprising: a pixel array having a plurality of pixels arrayed to form a plurality of rows and a plurality of columns; a scanning circuit configured to scan the plurality of rows of the pixel array in accordance with a selected mode of a plurality of modes; and a readout circuit configured to read out signals from pixels on a selected row in scanning by the scanning circuit, wherein the plurality of modes include a first mode of performing image capturing at a first frame rate and a second mode of performing image capturing at a second frame rate lower than the first frame rate, and the number of times of scanning on the plurality of rows by the scanning circuit in one frame period in the second mode is larger than the number of times of scanning on the plurality of rows by the scanning circuit in one frame period in the first mode.

Further features of the present invention will become apparent from the following description of exemplary embodiments with reference to the attached drawings.

DESCRIPTION OF THE EMBODIMENTS

The present invention will be described below through an exemplary embodiment with reference to the accompanying drawings. Note that radiation includes α-rays, β-rays, and γ-rays in addition to X-rays.

Figure 1:
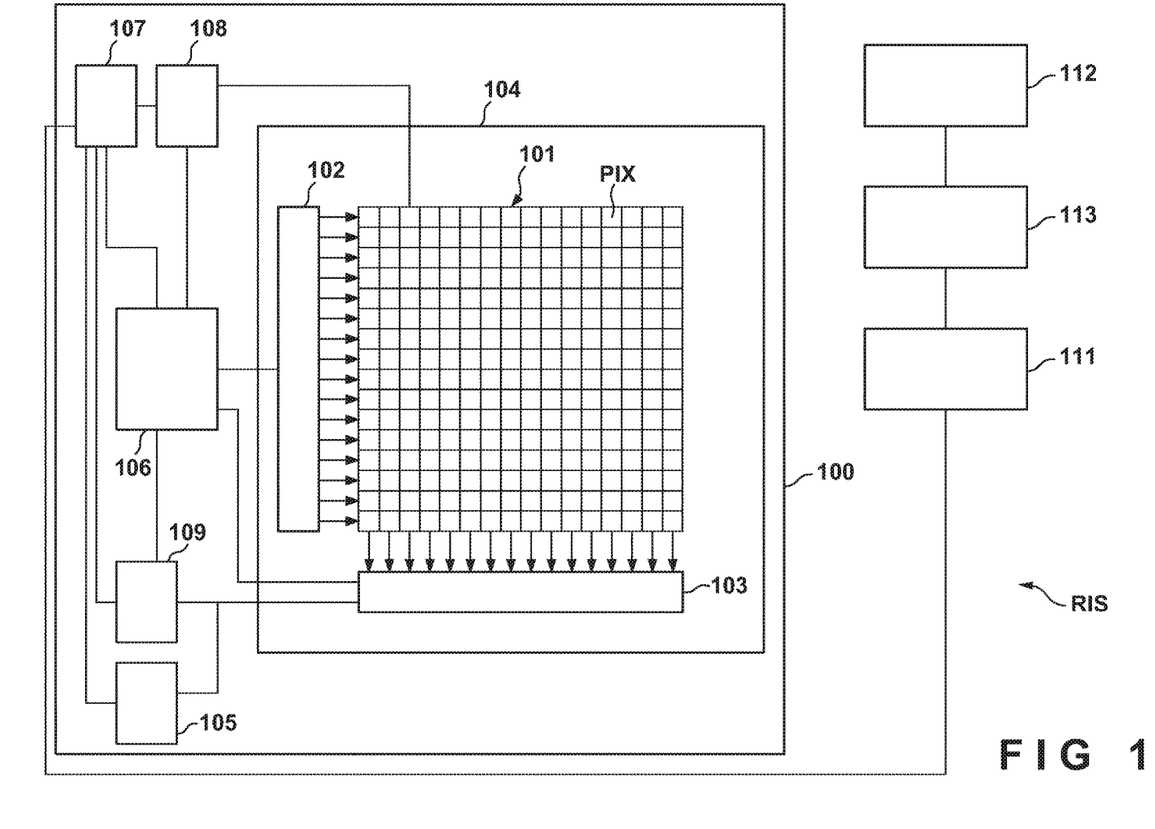
FIG. 1 is a block diagram showing the arrangement of a radiation imaging system according to an embodiment of the present invention.

FIG. 1 shows the arrangement of a radiation imaging system RIS according to an embodiment of the present invention. The radiation imaging system RIS obtains a radiation image of an object by irradiating the object with radiation such as X-rays and detecting X-rays transmitted through the object. The radiation imaging system RIS can include, for example, a radiation source 112, an exposure controller 113, a controller 111, and a radiation imaging apparatus 100. The exposure controller 113 causes the radiation source 112 to generate radiation in response to an exposure command issued by the operator. The controller 111 controls the radiation imaging apparatus 100 and obtains a radiation image from the radiation imaging apparatus 100. The controller 111 also controls the exposure controller 113.

The radiation imaging apparatus 100 can include an image capturing part 104 which captures a radiation image, a communication part 107 which performs communication with the controller 111, a controller 106 which controls the image capturing part 104, and a power supply part 108 which supplies power to the image capturing part 104. The radiation imaging apparatus 100 can also include an analyzer 109 which analyzes an image output from the image capturing part 104 and a processor 105 which arithmetically processes an image. Some of the constituent elements of the radiation imaging apparatus 100 may be incorporated in the controller 111. Alternatively, the radiation imaging apparatus 100 and the controller 111 may be integrated. For example, in the case shown in FIG. 1, the analyzer 109 and the processor 105 are incorporated in the radiation imaging apparatus 100. However, the analyzer 109 and the processor 105 may be incorporated in the controller 111.

The image capturing part 104 can include, for example, a pixel array 101, a scanning circuit 102, and a readout circuit 103. The pixel array 101 has a plurality of pixels arrayed to form a plurality of rows and a plurality of columns. The scanning circuit 102 scans a plurality of rows of the pixel array 101 in accordance with a mode selected from a plurality of modes (image capture modes). The readout circuit 103 reads out signals from the pixel array 101. More specifically, the readout circuit 103 reads out signals from pixels on a row, of the plurality of rows of the pixel array 101, which is selected by the scanning circuit 102 in a scanning operation. To read out signals from the pixel array 101 is to process signals output from the pixel array 101 and output signals corresponding to the processed signals.

Figure 2:
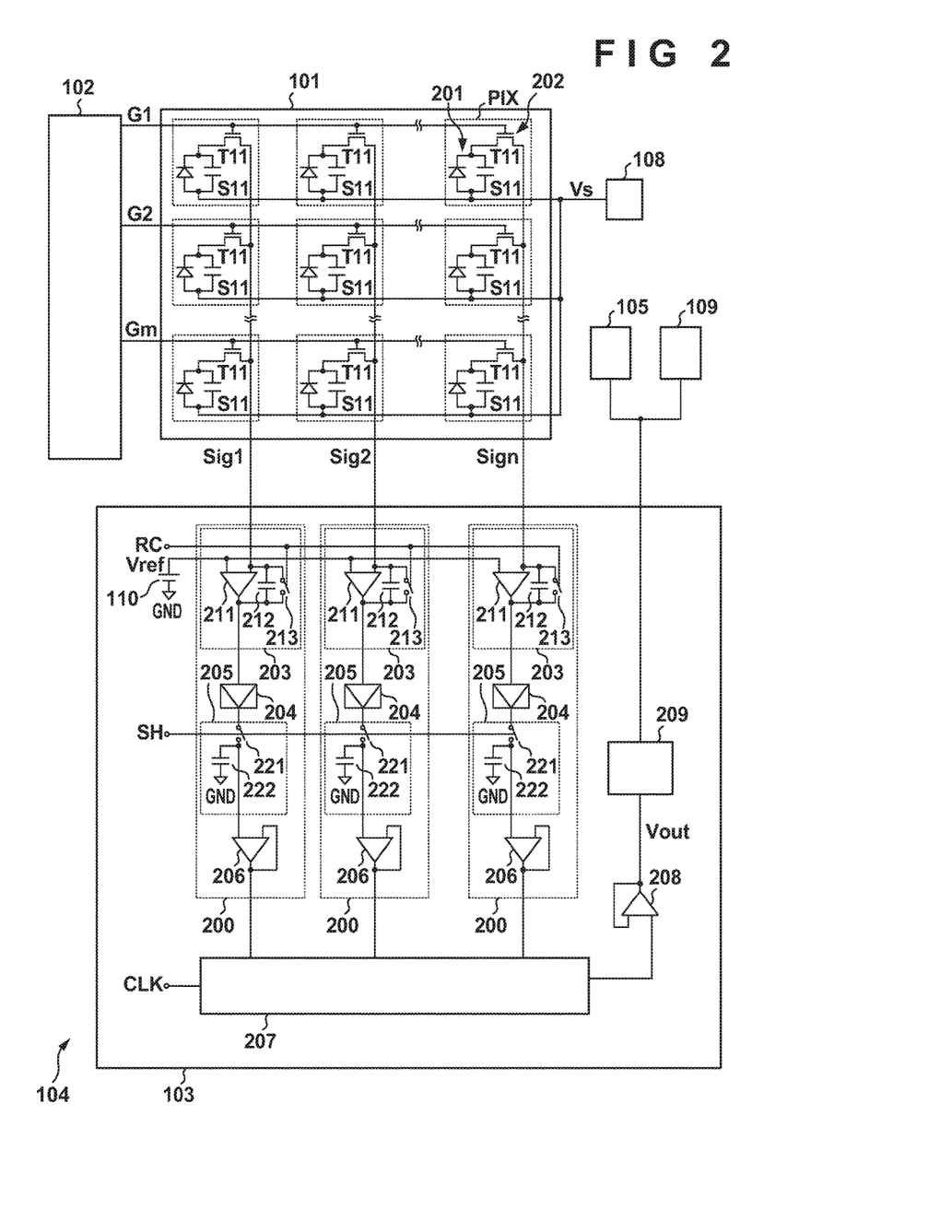
FIG. 2 is a circuit diagram exemplarily showing an equivalent circuit of an image capturing part of a radiation imaging apparatus in the radiation imaging system in FIG. 1.

FIG. 2 exemplarily shows an equivalent circuit of the image capturing part 104. A pixel PIX can include a conversion element 201 which converts radiation or light into charge and a switch element 202 which outputs an electrical signal corresponding to the charge. For example, the conversion element 201 is a photoelectric conversion element which converts light with which the conversion element 201 is irradiated into charge, and is a PIN photodiode or MIS photodiode made of amorphous silicon as a main material and arranged on an insulating substrate such as a glass substrate. In addition, it is possible to use, as the conversion element 201, an indirect conversion element including a wavelength converter which converts radiation into light in a wavelength region which can be detected by the photoelectric conversion element or a direct conversion element which directly converts radiation into charges.

It is possible to use, as the switch element 202, a transistor having a controller terminal and two main terminals, for example, a TFT (Thin-Film Transistor). One electrode of the conversion element 201 is electrically connected to one of the main terminals of the switch element 202, and the other electrode is electrically connected to the power supply part 108 via a common bias line Vs. Referring to FIG. 2, in order to discriminate the conversion elements 201 from each other, each conversion element 201 is assigned with the symbol "Sij" (i represents a row number, and j represents a column number). In addition, in order to discriminate the switch elements 202 from each other, each switch element 202 is assigned with the symbol "Tij" (i represents a row number, and j represents a column number).

The control terminals of the switch elements 202 of the plurality of pixels PIX constituting one row are connected to a drive line Gi (i represents a row number) of the corresponding row. For example, the control terminals of switch elements T11 to T1n of the plurality of pixels PIX constituting the first row are electrically connected to a drive line G1 of the first row. Therefore, the minimum unit of the plurality of pixels PIX of the pixel array 101 which are driven by the scanning circuit 102 is the pixels PIX constituting one row.

The other main terminal of each of the switch elements 202 of the plurality of pixels PIX constituting one column is connected to a signal line Sigj (j representing a column number) of the corresponding column. For example, the main terminals of switch elements T11 to Tm1 of the plurality of pixels PIX constituting the first column are electrically connected to a signal line Sig1 of the first column. While the switch elements 202 are in the conducting state, electrical signals corresponding to the charges of the conversion elements 201 are output to the readout circuit 103 via the signal line Sigj. A plurality of signal lines Sig1 to Sign are electrically connected to the readout circuit 103.

The readout circuit 103 includes a plurality of amplifier circuits 200 which respectively amplify a plurality of electrical signals output in parallel from the pixel array 101 via the plurality of signal lines Sig1 to Sign. Each amplifier circuit 200 can include an integration amplifier 203, a variable amplifier 204, a sample/hold circuit 205, and a buffer amplifier 206. The integration amplifier 203 amplifies electrical signals output via the signal line Sigj. The variable amplifier 204 amplifies electrical signals from the integration amplifier 203. The sample/hold circuit 205 samples and holds electrical signals from the variable amplifier 204. The buffer amplifier 206 buffers electrical signals from the sample/hold circuit 205.

The integration amplifier 203 can include, for example, an operational amplifier 211, an integration capacitor 212, and a reset switch 213. The operational amplifier 211 has an inverting input terminal which receives an electrical signal provided via the signal line Sigj, a non-inverting input terminal which receives a reference voltage Vref from a reference power supply 110, and an output terminal. The integration capacitor 212 and the reset switch 213 are arranged in parallel between the inverting input terminal and the output terminal. The integration capacitor 212 can have a variable capacitance value Cf. The sample/hold circuit 205 can be constituted by, for example, a sampling switch 221 and a sampling capacitor 222.

The readout circuit 103 can further include a multiplexer 207, a buffer amplifier 208, and an A/D converter 209. The multiplexer 207 sequentially selects electrical signals output in parallel from the plurality of amplifier circuits 200, and outputs them as image signals. The buffer amplifier 208 impedance-converts an image signal output from the multiplexer 207 and outputs an analog electrical signal as an image signal Vout. The A/D converter 209 converts the image signal Vout output from the buffer amplifier 208 into digital image data and provides it to the processor 105 and the analyzer 109.

The scanning circuit 102 generates driving signals Gi and outputs them to drive lines Gi in accordance with control signals D-CLK, OE, and DIO supplied from the controller 106. Note that in this specification, each signal line and a signal output to the signal line are assigned with the same reference symbol. Each driving signal Gi has a conducting voltage Vcom which sets the switch element 202 of the pixel PIX in the conducting state or a non-conducting voltage Vss which sets the switch element 202 in the non-conducting state.

For example, the scanning circuit 102 can include a shift register. The control signal D-CLK is a shift clock which causes the shift register to perform a shift operation. The control signal DIO is a pulse transferred by the shift register. The control signal OE is a signal for controlling the output terminal of the shift register. In addition, the controller 106 controls the readout circuit 103 by supplying control signals RC, SH, and CLK to the readout circuit 103. In this case, the control signal RC controls the reset switch 213 of the integration amplifier 203, the controls signal SH controls the sampling switch 221 of the sample/hold circuit 205, and the control signal CLK controls the multiplexer 207.

Figure 3:
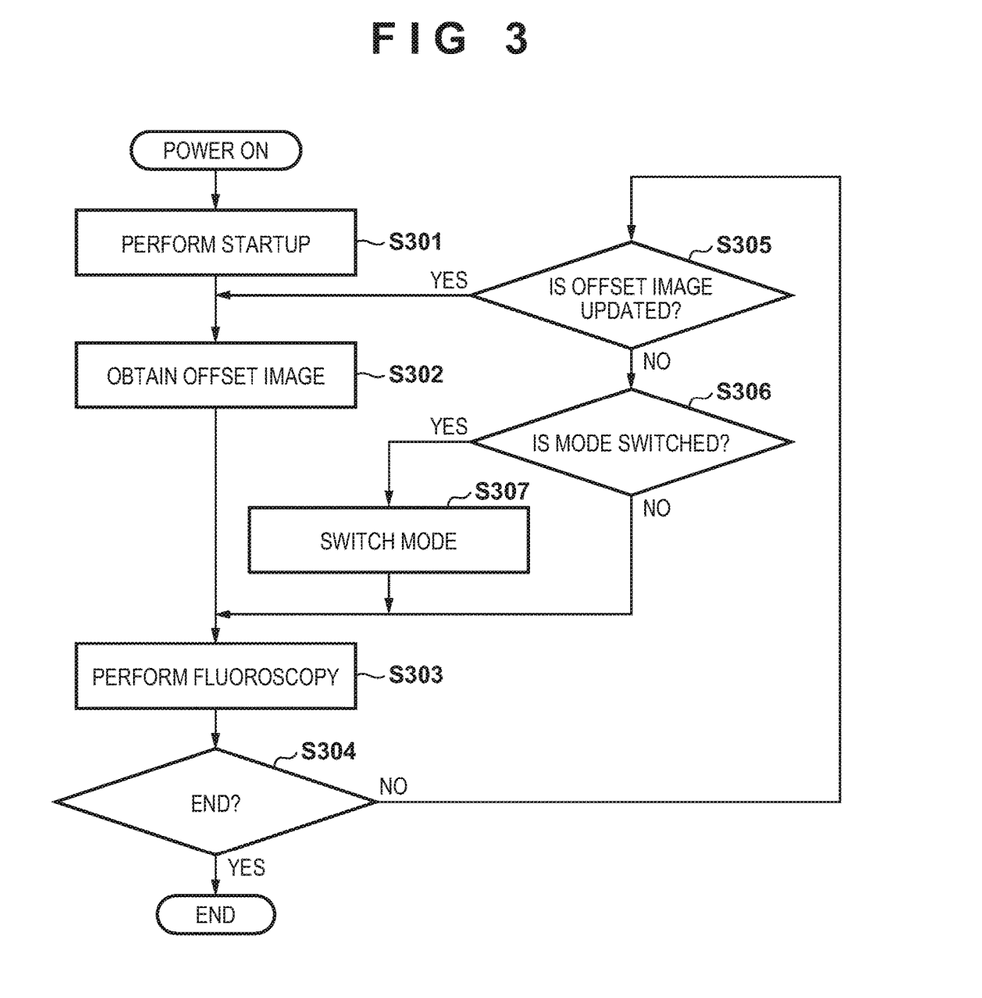
FIG. 3 is a flowchart exemplarily showing a method of operating the radiation imaging system and the radiation imaging apparatus in FIG. 1.

FIG. 3 exemplarily shows a method of operating the radiation imaging system RIS and the radiation imaging apparatus 100. When the power supply of the radiation imaging apparatus 100 is turned on, the radiation imaging apparatus 100 performs a startup operation for stabilizing the operation of the radiation imaging apparatus 100 in step S301. The controller 106 can control this operation. In the startup operation, a reset operation can be performed to remove charges accumulated originating from dark currents. The reset operation is the operation of resetting the charges accumulated in the conversion element 201 by setting the switch element 202 in the conducting state. The reset operation is performed for at least each of the plurality of rows constituting the pixel array 101 by causing the scanning circuit 102 to scan. For example, in a reset operation, the reset switch 213 is set in the conducting state to set the operational amplifier 211 in the voltage follower state, thereby fixing the signal line Sigj to the reference voltage Vref. In this state, setting the switch element 202 in the conducting state will remove charges accumulated in the conversion element 201 and reset the voltage of the conversion element 201.

In step S302, an offset image is obtained. The controller 106 can control this operation. An offset image is obtained by performing an image capturing operation without irradiating the radiation imaging apparatus 100 with radiation. An offset image is obtained by performing image capturing a plurality of times (for example, 30 times) and processing (for example, averaging) the obtained images. An image capturing operation includes accumulating charges in a plurality of pixels PIX of the pixel array 101, causing the scanning circuit 102 to sequentially select (scanning) a plurality of rows of the pixel array 101, and causing the readout circuit 103 to read out signals from the pixels PIX on each selected row.

The radiation imaging apparatus 100 has a plurality of modes (image capture modes). The controller 106 can be notified of information for designating a mode via the controller 111 operated by the operator. The plurality of modes differ in at least a frame rate (the number of frames obtained per unit time (an image capturing count)), the signal amplification factor (gain) of the readout circuit 103, a pixel sum (binning), or an image capturing range. The plurality of modes include, for example, the first mode of capturing a radiation image at the first frame rate and the second mode of capturing a radiation image at the second frame rate lower than the first frame rate. In other words, the first mode is a mode of capturing a 1-frame radiation image in the first period, and the second mode is a mode of capturing a 1-frame radiation image in the second period longer than the first period. The plurality of modes can include one or a plurality of modes other than the first and second modes.

Offset images are obtained for the respective modes. For example, the controller 106 executes control to obtain an offset image while the first mode is set and to obtain an offset image while the second mode is set.

After an offset image is obtained in step S302, the controller 106 executes fluoroscopy (moving image capturing) in a mode set by the operator in step S303. More specifically, the controller 106 repeats an image capturing operation in accordance with the frame rate, signal amplification factor (gain), pixel sum (binning), and image capturing range defined in the mode set by the operator. In fluoroscopy, the radiation imaging apparatus 100 is intermittently irradiated with radiation from the radiation source 112 to repeat an image capturing operation in synchronism with irradiation with radiation.

In this case, when performing fluoroscopy over a long time, offset components included in an image captured by the radiation imaging apparatus 100 change with a change in environmental temperature or the like, resulting in failure to perform proper offset correction. As a consequence, artifacts can be formed in an image. In step S305, the controller 106 decides whether to update an offset image. The controller 106 may decide to update an offset image in accordance with a fluoroscopy time, a temperature, and the like or in accordance with an instruction from the operator. Upon deciding to update an offset image, the process returns to step S302 to obtain an offset image again. When obtaining an offset image again, the radiation source 112 stops intermittent irradiation with radiation. Upon completion of re-obtaining of an offset image, the process returns to fluoroscopy in step S303.

Fluoroscopy can be terminated at any time. It is also possible to switch a mode during fluoroscopy. When terminating fluoroscopy, the radiation source 112 stops intermittent irradiation with radiation, and the radiation imaging apparatus 100 stops an image capturing operation. When the operator issues an instruction to switch a mode, the controller 111 sends a command requesting to switch the mode to the controller 106 of the radiation imaging apparatus 100. In step S307, the controller 106 switches the mode in accordance with the command from the controller 111. In addition, when the operator issues an instruction to switch the mode to the controller 111, the controller 111 sends a command to cause the radiation source 112 to temporarily stop generating radiation to the exposure controller 113, and temporarily stops generating radiation. When the radiation imaging apparatus 100 switches the mode to set a state in which fluoroscopy can be resumed, the controller 111 sends a command to cause the radiation source 112 to start irradiation with radiation with respect to the exposure controller 113. In step S303, fluoroscopy is started in a new mode. Upon receiving a command to switch a mode while the controller 106 of the radiation imaging apparatus 100 reads out an image of a given frame from the readout circuit 103, the controller 106 switches the mode upon reading out an image of the frame.

As described above, it is known that offset components transiently change immediately after mode switching. In addition, since a transient change continues for a relatively long time, even if an offset image is prepared for offset correction in a transient state, it is difficult to perform proper offset correction. Artifacts are superimposed on output images.

The present inventor confirmed that offset components which transiently change have a correlation with the difference (change amount) between frame rates before and after mode switching. More specifically, when the difference between frame rates before and after mode switching is large, offset components which transiently change are large, and it takes a long time until the end of the transient change. In contrast to this, when the difference between frame rates before and after mode switching is small, offset components which transiently change are small, and it takes a short time until the end of the transient change.

Figure 4:
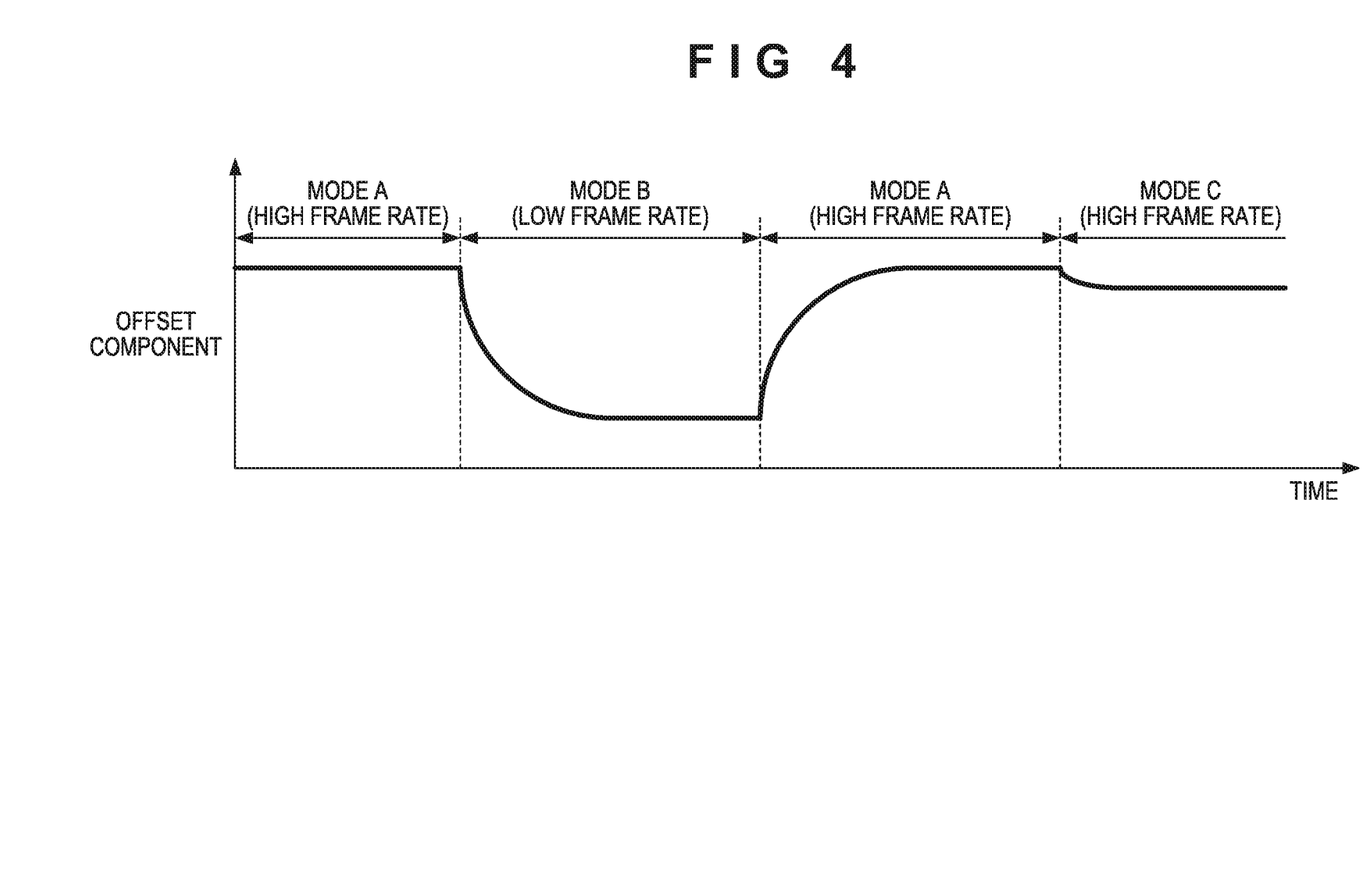
FIG. 4 is a graph exemplarily showing transient changes in offset components accompanying mode switching.

FIG. 4 exemplarily shows transient changes in offset components accompanying mode switching. Modes A and C are high frame rate modes having the same frame rate. Mode B is a low frame rate mode having a lower frame rate than modes A and C. Transient changes in offset components immediately after the switching of mode A to mode B and immediately after the switching of mode B to mode A are large, and it takes long times until the ends of the changes. In contrast to this, when mode A switches to mode C, which is mode switching without a change in frame rate, a transient change in offset components is small, and it takes a short time until the end of the change. Mode A and mode C are, for example, modes which have the same frame rate while differing in the signal amplification factor (gain) of the readout circuit 103 or pixel sum (binning).

It seems from the above results that the magnitude of a transient change in offset components accompanying mode switching has a strong correlation with the toggle count of each switch element 202 per unit time, in other words, the number of times of scanning on the pixel array 101 by the scanning circuit 102 per unit time. The toggling of the switch element 202 indicates the ON/OFF operation of the switch element 202. To make the scanning circuit 102 scan the pixel array 101 is to sequentially select a plurality of rows of the pixel array 101 and switch the switch elements 202 of the pixels PIX on each selected row from the OFF state (non-conducting state) to the ON state (conducting state).

That is, it is possible to suppress a change in offset components accompanying mode switching by preventing the number of times of scanning on the pixel array 101 by the scanning circuit 102 per unit time from changing accompanying mode switching. The scanning circuit 102 scans the pixel array 101 both when resetting the pixels PIX (conversion elements 201) and when reading out signals from the pixels PIX. For this reason, increasing the number of times of resetting per frame in a low frame rate mode can reduce a change in offset components which is caused by mode switching accompanying a change in frame rate, if ever.

Figure 5:
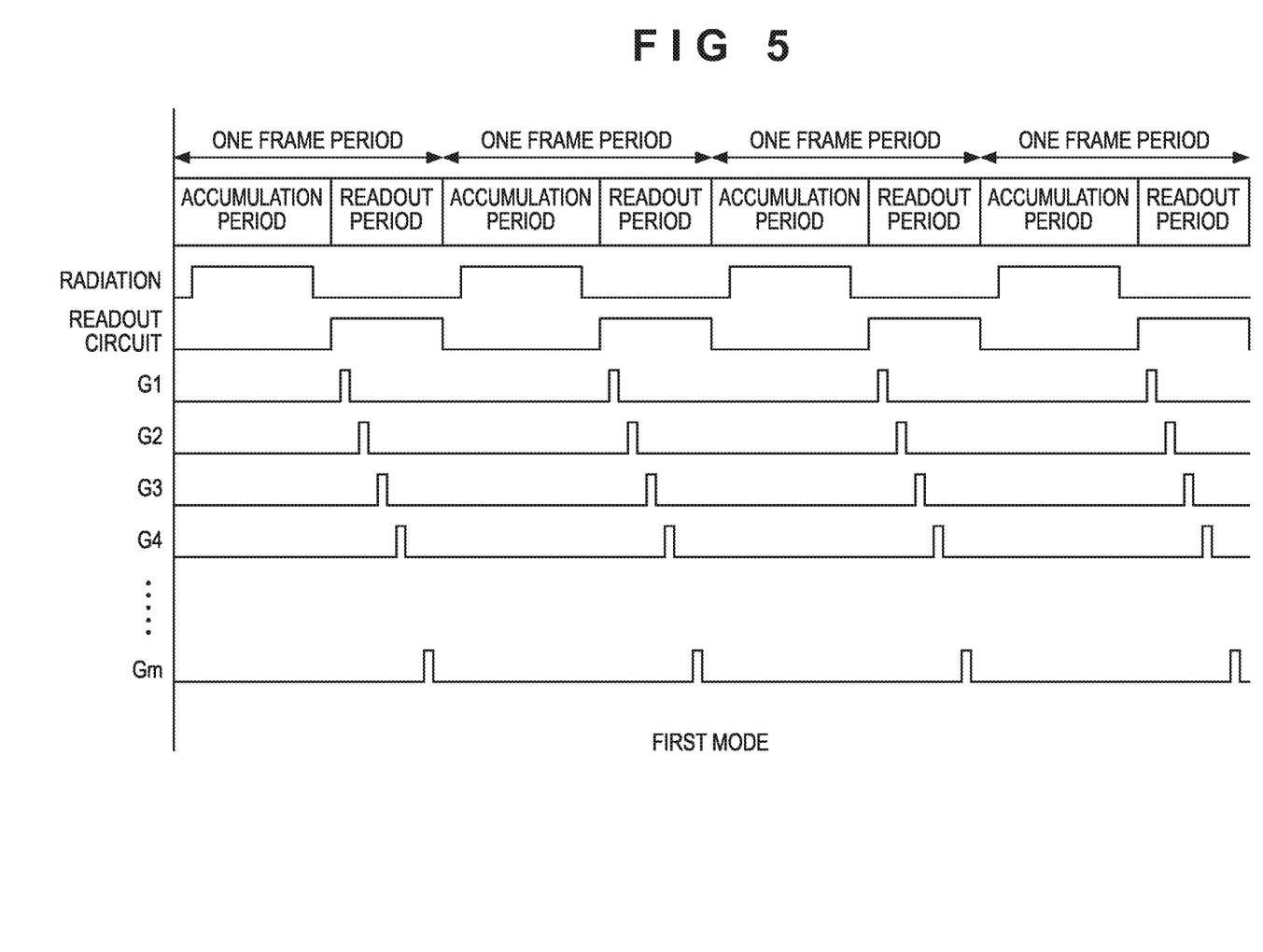
FIG. 5 is a timing chart exemplarily showing an operation in the first mode.
Figure 6:
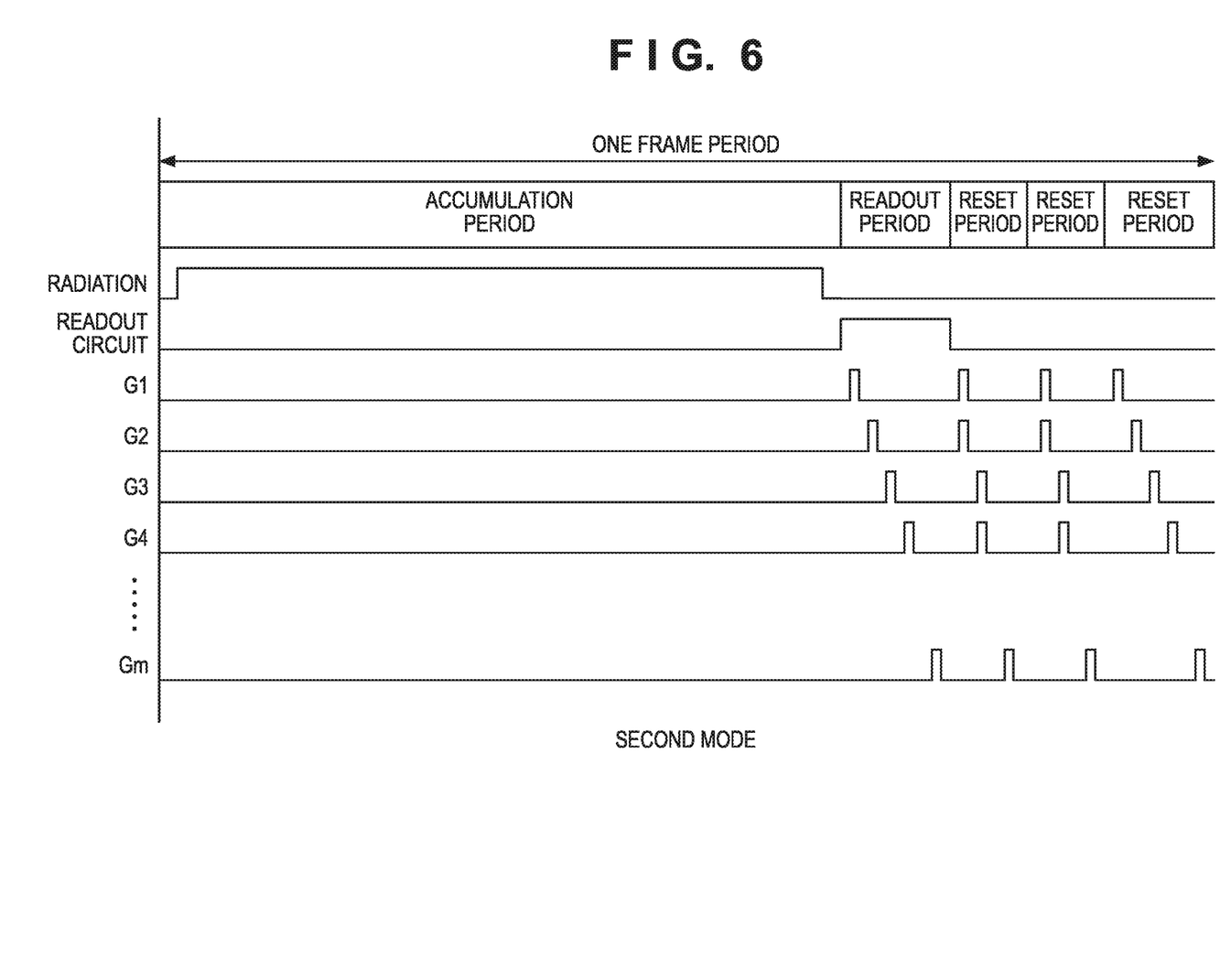
FIG. 6 is a timing chart exemplarily showing an operation in the second mode.

FIGS. 5 and 6 exemplarily show operations in two modes based on the above idea. Consider here the first mode of capturing a radiation image at the first frame rate and the second mode of capturing a radiation image at the second frame rate lower than the first frame rate. FIG. 5 exemplarily shows an operation in the first mode. FIG. 6 exemplarily shows an operation in the second mode. The operation in the first mode will be described first. One frame period in the first mode includes an accumulation period in which signals corresponding to applied radiation are accumulated in the plurality of pixels PIX and a readout period in which the readout circuit 103 reads out signals corresponding to one frame from the pixel array 101 while the scanning circuit 102 scans a plurality of rows. An operation in a readout period is called an accumulation operation. An operation in a readout period is called a readout operation. During an accumulation period, the non-conducting voltage Vss is applied to the switch elements 202 of all the pixels PIX, and hence the switch elements 202 of all the pixels PIX are in the non-conducting state. When an accumulation period is over, the period shifts to a readout period. During the readout period, the readout circuit 103 reads out signals from the plurality of pixels PIX of the pixel array 101 while the scanning circuit 102 scans a plurality of rows of the pixel array 101. Scanning performed by the scanning circuit 102 is the operation of sequentially selecting drive lines from the drive line G1 of the first row to the drive line Gm of the mth row. That is, during a readout period, the scanning circuit 102 sequentially supplies the conducting voltage Vcom to drive lines from the drive line G1 of the first row to the drive line Gm of the mth row (that is, rows are sequentially selected from the first row to the mth row), and the readout circuit 103 reads out signals from the pixels PIX of each selected row. In the above manner, in the first mode, only one scan is performed on a plurality of rows of the pixel array 101 during one frame period.

An operation in the second mode will be described next. One frame period in the second mode includes an accumulation period in which signals corresponding to applied radiation are accumulated in the plurality of pixels PIX and a readout period in which the readout circuit 103 reads out signals corresponding to one frame from the pixel array 101 while the scanning circuit 102 scans a plurality of rows. One frame period in the second mode includes one or a plurality of reset periods. One reset period is a period in which the scanning circuit 102 scans a plurality of rows of the pixel array 101 so as to reset the plurality of pixels PIX of the pixel array 101. An operation in a reset period is called a reset operation.

An accumulation period in the second mode is longer than that in the first mode. For this reason, the frame rate in the second mode is lower than that in the first mode. Therefore, if one frame period in the second mode includes only an accumulation period and a readout period, the number of times of scanning on the pixel array 101 per unit time is smaller than that in the first mode. In the second mode, therefore, one frame period includes a reset period in addition to an accumulation period and a readout period. As a consequence, the number of times of scanning on a plurality of rows of the pixel array 101 by the scanning circuit 102 in one frame period in the second mode is larger than the number of times of scanning on a plurality of rows of the pixel array 101 by the scanning circuit 102 in one frame period in the first mode.

In moving image capturing, since a plurality of frame periods are continuous, a reset period may be provided after a readout period or before an accumulation period. A readout operation in a readout period in the second mode is similar to a readout operation in the first mode. During a reset period, the scanning circuit 102 scans drive lines from the drive line G1 of the first row to the drive line Gm of the mth row. That is, during a reset period, the scanning circuit 102 sequentially supplies the conducting voltage Vcom to drive lines from the drive line G1 of the first row to the drive line Gm of the mth row (that is, rows are sequentially selected from the first row to the mth row) to reset the conversion elements 201 of the selected pixels PIX on each selected row.

When one frame period in the second mode includes a plurality of reset periods, the scanning time in the last reset period of the plurality of reset periods (the time required for the scanning circuit 102 to scan a plurality of rows of the pixel array 101) is preferably equal to the scanning time in a readout period in the second mode (the time required for the scanning circuit 102 to scan a plurality of rows of the pixel array 101). More specifically, the number of rows simultaneously selected in a reset period is preferably equal to that in a readout period while the time (line time) from the start of selection of a given row to the start of selection of the next row in the reset period is preferably equal to that in the readout period.

If the scanning time in the last reset period is different from that in the subsequent readout period, the time from the resetting of the ith row in the last reset period to the readout of the ith row in the subsequent readout period varies between a plurality of rows. For this reason, artifact components (for example, a dark current and a residual image) superimposed by time integration vary between the respective rows. As a result, artifacts are superimposed on an image or it becomes difficult to perform artifact correction.

Artifacts can be reduced or easily corrected by equalizing the scanning time in the last reset period with the scanning time in the subsequent readout period. This makes it possible to provide high-quality images.

In addition, the scanning time in a reset period before the last reset period of the plurality of reset periods in one frame period is preferably shorter than that in the last reset period. For example, the scanning time in a reset period before the last reset period of the plurality of reset periods in one frame period is preferably ⅕ or less that in the last reset period. Alternatively, the scanning circuit 102 may scan a plurality of rows of the pixel array 101 in increments of at least two rows in a reset period before the last reset period of the plurality of reset periods in one frame period. Such control is advantageous in shortening the scanning time and increasing the number of times of scanning, and is advantageous in reducing the difference in the number of times of scanning per unit time between modes.

It is ideal that there is no difference in the number of times of scanning per unit time between modes. However, if the difference in the number of times of scanning per unit time between the first mode with a high frame rate and the second mode with a low frame rate is reduced by inserting a reset period in one frame period in the low frame rate mode, an equivalent effect can be obtained.

As described above, it is possible to reduce a transient change in offset components at the time of mode switching by inserting a reset period in a frame period in a mode having a lower frame rate than the other mode so as to reduce the difference in the number of times of scanning per unit time between the modes. This makes it possible to shorten the time required to obtain a large quantity of offset images for offset correction for images at the time of transient changes and reduce the memory area required to hold the offset images.

According to the above description, inserting a reset period in one frame period in a low frame mode will reduce the difference in the number of times of scanning per unit time between the first mode with a high frame rate and the second mode with a low frame mode. However, a similar effect can also be obtained by inserting a dummy readout period in one frame period. A dummy readout period can be the same as a normal readout period, but signals read out by the readout circuit 103 in the dummy readout period will not be used in general. Alternatively, a scanning period in which a plurality of rows are scanned without resetting the pixels PIX may be inserted in one frame period. Alternatively, at least one of a reset period, a dummy readout period, and a scanning period may be inserted in one frame period. Alternatively, at least one of a dummy readout period and a scanning period may be inserted in one frame period, and a reset period may be inserted thereafter.

The operation of the radiation imaging apparatus having three or more modes will be described below.

Figure 7:
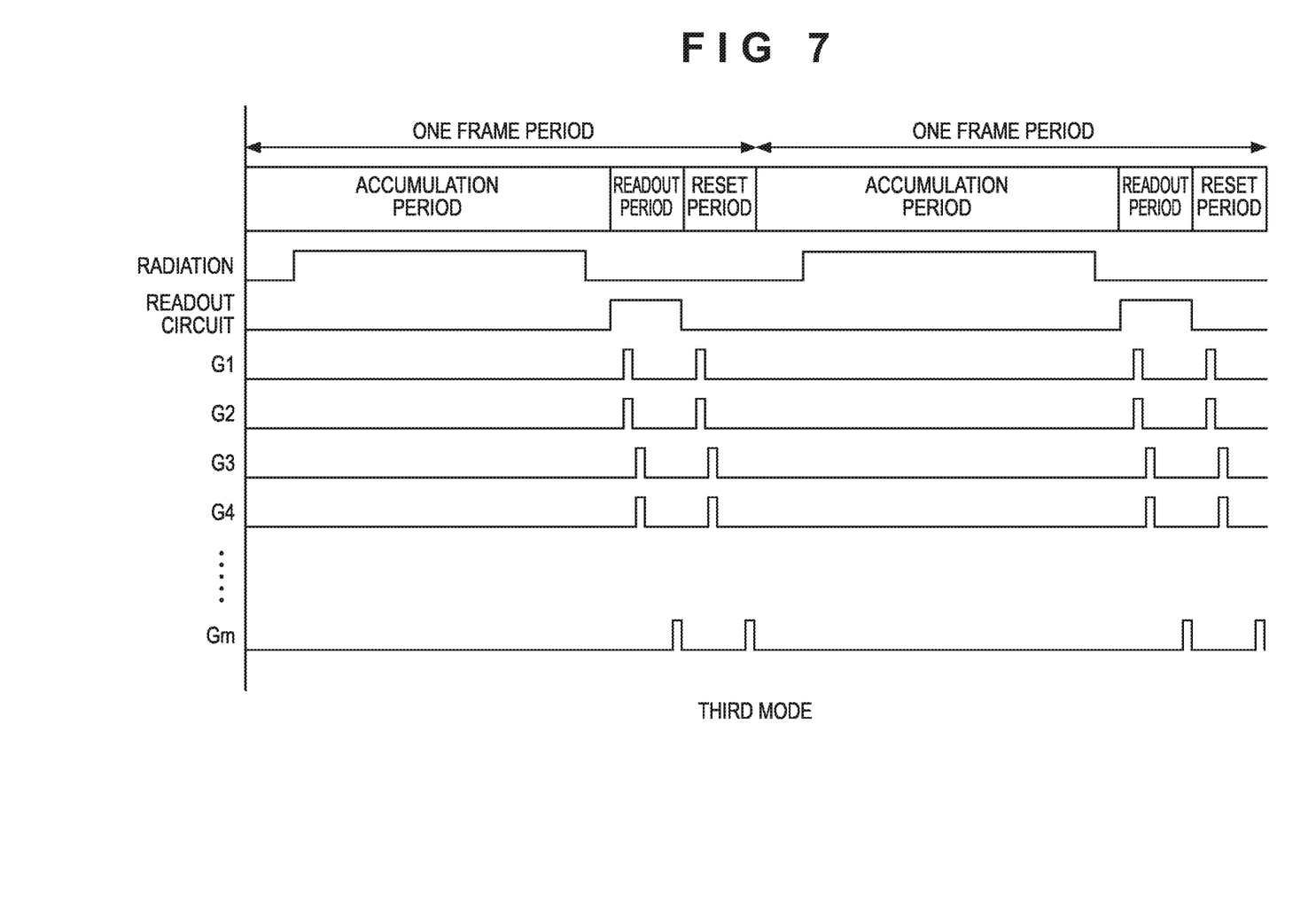
FIG. 7 is a timing chart exemplarily showing an operation in the third mode.

Described first is the operation of the radiation imaging apparatus 100 having the first, second, and third modes, with the magnitude relationship between the frame rates of the respective modes being expressed by first mode>third mode>second mode. Assume that the first and second modes have the relationship described above. FIG. 7 exemplarily shows an operation in the third mode. In the third mode, the number of times of resetting is one. The number of times of resetting in one frame period in the third mode is preferably larger than that in one frame period in the second mode and smaller than that in one frame period in the first mode. The numbers of times of resetting are decided to reduce or preferably eliminate the difference in the number of times of scanning per unit time between the first, second, and third modes. Since the number of times of resetting in third mode shown in FIG. 7 is one, the scanning time in a reset period is preferably equal to that in a readout period. More specifically, the number of rows simultaneously selected in scanning in a reset period is preferably equal to that in a readout period while the time (line time) from the start of selection of a given row to the start of selection of the next row in the reset period is preferably equal to that in the readout period. As described above, such control can reduce artifacts or allows easy correction of them, and is advantageous in providing high-quality images.

Described next is the operation of the radiation imaging apparatus 100 having the first, second, and fourth modes, with the magnitude relationship between the frame rates of the respective modes being expressed by first mode≅fourth mode>second mode. Assume that the first and second modes have the relationship described above. An operation in the fourth mode is basically the same as that in the first mode, and does not require any reset operation like that executed in the second mode. This is because, even when mode switching is performed from the first mode to the fourth mode, reducing the frame rate difference will also reduce artifacts originating from transiently changing components.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefits of Japanese Patent Application No. 2016-066316 filed Mar. 29, 2016, and Japanese Patent Application No. 2016-135207 filed Jul. 7, 2016, which are hereby incorporated by reference herein in their entirety.

What is claimed is:

1. A radiation imaging apparatus comprising:
a pixel array having a plurality of pixels arrayed to form a plurality of rows and a plurality of columns;
a scanning circuit configured to scan the plurality of rows of the pixel array in accordance with a selected mode of a plurality of modes including a first mode of capturing at a first frame rate a plurality of radiation images formed on the pixel array by irradiated radiation, and a second mode of capturing at a second frame rate a plurality of radiation images formed on the pixel array by irradiated radiation; and
a readout circuit configured to read out signals from pixels on a selected row in scanning by the scanning circuit, wherein
the second frame rate is lower than the first frame rate, and
the number of times of scanning on the plurality of rows by the scanning circuit in one frame period for capturing one radiation image formed on the pixel array by irradiated radiation in the second mode is larger than the number of times of scanning on the plurality of rows by the scanning circuit in one frame period for capturing one radiation image formed on the pixel array by irradiated radiation in the first mode, such that a difference in the number of times of scanning by the scanning circuit per unit time between the first mode and the second mode is reduced.

2. The apparatus according to claim 1, wherein one frame period in the first mode includes an accumulation period in which the plurality of pixels accumulate signals corresponding to irradiated radiation, and a readout period in which the readout circuit reads out signals corresponding to the accumulated signals from the pixel array while the scanning circuit scans the plurality of rows, and
one frame period in the second mode includes an accumulation period in which the plurality of pixels accumulate signals corresponding to irradiated radiation, a readout period in which the readout circuit reads out signals corresponding to the accumulated signals from the pixel array while the scanning circuit scans the plurality of rows, and a reset period in which the scanning circuit scans the plurality of rows so as to reset the plurality of pixels.

3. The apparatus according to claim 2, wherein one frame period in the second mode includes a plurality of reset periods including the reset period.

4. The apparatus according to claim 3, wherein a time required for the scanning circuit to scan the plurality of rows in a last reset period of the plurality of reset periods in the second mode is equal to a time required for the scanning circuit to scan the plurality of rows in the readout period in the second mode.

5. The apparatus according to claim 4, wherein the number of rows simultaneously selected by the scanning circuit remains the same when the scanning circuit scans the plurality of rows in the last reset period of the plurality of reset periods in the second mode and when the scanning circuit scans the plurality of rows in the readout period in the second mode.

6. The apparatus according to claim 4, wherein a time from a start of selection of a given row to a start of selection of a next row remains the same between a case in which the scanning circuit scans the plurality of rows in the last reset period of the plurality of reset periods in the second mode and a case in which the scanning circuit scans the plurality of rows in the readout period in the second mode.

7. The apparatus according to claim 4, wherein the scanning circuit scans the plurality of rows in increments of at least two rows in a reset period before the last reset period of the plurality of reset periods.

8. The apparatus according to claim 3, wherein a time required for the scanning circuit to scan the plurality of rows in a reset period before the last reset period of the plurality of reset periods is shorter than a time required for the scanning circuit to scan the plurality of rows in the last reset period.

9. The apparatus according to claim 1, further comprising a controller configured to switch one of the first mode and the second mode to the other of the first mode and the second mode when capturing a moving image.

10. A radiation imaging system comprising:
a radiation source configured to generate radiation; and
the radiation imaging apparatus defined in claim 1.

11. A method of operating a radiation imaging apparatus comprising a pixel array having a plurality of pixels arrayed to form a plurality of rows and a plurality of columns, a scanning circuit configured to scan the plurality of rows of the pixel array in accordance with a selected mode of a plurality of modes, and a readout circuit configured to read out signals from pixels on a selected row in scanning by the scanning circuit, comprising the steps of:
performing a first mode of capturing at a first frame rate a plurality of radiation images formed on the pixel array by irradiated radiation;
performing a second mode of capturing at a second frame rate a plurality of radiation images formed on the pixel array by irradiated radiation, wherein
the second frame rate is lower than the first frame rate, and
the number of times of scanning on the plurality of rows by the scanning circuit in one frame period for capturing one radiation image formed on the pixel array by irradiated radiation in the second mode is larger than the number of times of scanning on the plurality of rows by the scanning circuit in one frame period for capturing one radiation image formed on the pixel array by irradiated radiation in the first mode, such that a difference in the number of times of scanning by the scanning circuit per unit time between the first mode and the second mode is reduced.

12. The method according to claim 11, wherein one frame period in the first mode includes an accumulation period in which the plurality of pixels accumulate signals corresponding to irradiated radiation, and a readout period in which the readout circuit reads out signals corresponding to the accumulated signals from the pixel array while the scanning circuit scans the plurality of rows, and
one frame period in the second mode includes an accumulation period in which the plurality of pixels accumulate signals corresponding to irradiated radiation, a readout period in which the readout circuit reads out signals corresponding to the accumulated signals from the pixel array while the scanning circuit scans the plurality of rows, and a reset period in which the scanning circuit scans the plurality of rows so as to reset the plurality of pixels.

* * * * *